United States Patent
Aurelius et al.

(10) Patent No.: US 6,612,697 B1
(45) Date of Patent: Sep. 2, 2003

(54) PROTECTIVE EYEWEAR LENS

(75) Inventors: Michael J. Aurelius, Royalton, MN (US); Robert N. Aurelius, Sauk Rapids, MN (US)

(73) Assignee: Aura Lens Products, Inc., Sauk Rapids, MN (US)

( * ) Notice: Subject to any disclaimer, the term of this patent is extended or adjusted under 35 U.S.C. 154(b) by 361 days.

(21) Appl. No.: 09/775,371

(22) Filed: Feb. 1, 2001

(51) Int. Cl.[7] ................................................. G02C 7/10
(52) U.S. Cl. ........................... 351/163; 351/44; 351/165
(58) Field of Search ................. 351/163, 164, 351/165, 44

(56) References Cited

U.S. PATENT DOCUMENTS

| 3,269,267 A | | 8/1966 | Collins |
| 3,850,502 A | | 11/1974 | Bloom |
| 3,959,171 A | * | 5/1976 | Woodcock ................... 501/50 |
| 4,311,368 A | | 1/1982 | Saito et al. |
| 4,320,939 A | | 3/1982 | Mueller |
| 4,679,918 A | | 7/1987 | Ace |
| 4,698,374 A | | 10/1987 | Gallas |
| 4,818,095 A | | 4/1989 | Takeuchi |
| 5,135,298 A | | 8/1992 | Feltman |
| 5,162,825 A | | 11/1992 | Kamekura et al. |
| 5,694,240 A | | 12/1997 | Sternbergh |
| 5,793,465 A | | 8/1998 | Gupta et al. |
| RE36,049 E | | 1/1999 | Kamekura et al. |
| 5,922,246 A | | 7/1999 | Matsushita et al. |
| 5,926,310 A | * | 7/1999 | Tamura et al. .............. 359/350 |
| 5,949,518 A | | 9/1999 | Belmares et al. |

* cited by examiner

Primary Examiner—Scott J. Sugarman
(74) Attorney, Agent, or Firm—Haugen Law Firm PLLP

(57) ABSTRACT

The present invention is directed to industrial eyewear lens systems for radiation protection of the human eye. The base material in combination with an infrared absorbing filter significantly reduces or eliminates the transmission of certain eye-damaging ultraviolet and infrared radiation. As a result, the vision of the lens wearer is not impaired, and the wearer is able to more readily visualize his or work, particularly in an industrial setting.

6 Claims, 4 Drawing Sheets

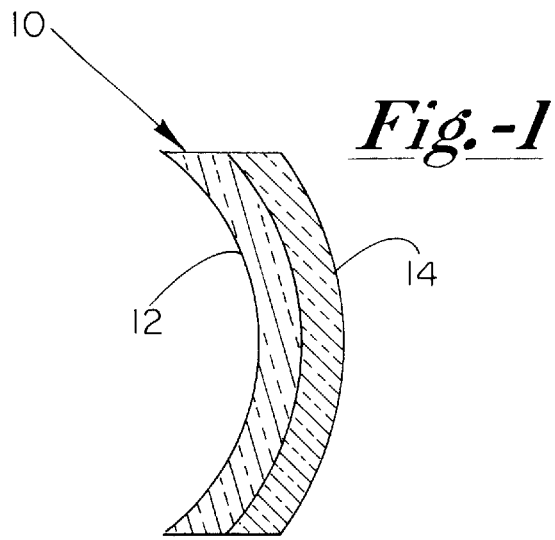
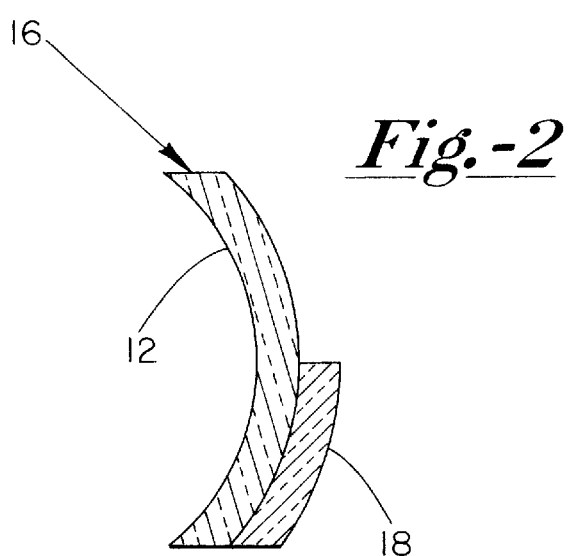
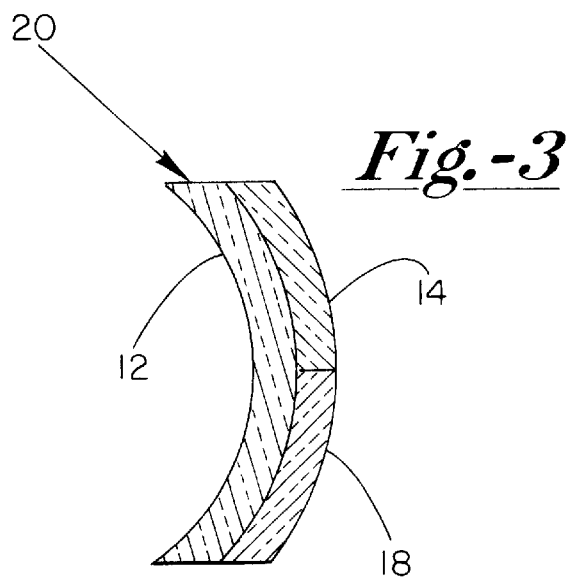

PROTECTIVE EYEWEAR LENS

FIELD OF THE INVENTION

The present invention relates to a lens combination for protective eyewear for industrial workers, the lens arrangements reducing or eliminating the transmission of eye-damaging wavelengths to the wearer, thus preventing impairment of the vision of the lens wearer while facilitating visualization of work, particularly in certain industrial settings.

BACKGROUND OF THE INVENTION

The ill effects to the human eye due to the absorption of radiation emitted by artificial light sources has received increasing attention. Optical effects can be particularly detrimental to industrial workers in vocations such as welding or glass-blowing, where visual exposure to damaging radiation may be intensified. Acute exposure is believed to result in corneal and/or retinal burns, while chronic exposure may produce corneal or lenticular opacities (cataracts).

General tissue damage to various parts of the eye has resulted from exposure to varying wavelengths across the entire spectrum. Retinal damage is possible in the visible and near infrared range (400 to 1400 nanomenters). Due to the focusing effects of the cornea and lens, the incident corneal radiant exposure at the retina will be increased by about 100,000 times.

Light in the ultraviolet (UV) and far infrared (IR) spectra produces harmful ocular effects principally at the cornea, although radiation at certain wavelengths may reach the lens and cause damage to that structure.

Actinic UV radiation at short wavelengths in the range of from 200 to 315 nanometers is responsible for what has been termed "welders flash" or photokeratitis. These are also the wavelengths responsible for sunburn in humans. Near UV radiation between 315 and 400 nanometers is particularly absorbed in the lens and may contribute to some forms of cataract.

Middle IR, between 1400 and 3000 nanometers, penetrates more deeply into the eye, and may contribute significantly to what has been termed "glass blower's cataract". Extensive exposure to near IR may also contribute to such cataracts.

Radiation at visible (400 to 780 nanometers) and near IR (780 to 1400 nanometers) is transmitted through the ocular media with little loss and usually is focused on a spot on the retina 10 to 20 microns in diameter. Such focusing may create intensities high enough to damage the retina. Wavelengths between 400 and 550 nanometers become particularly hazardous over long-term retinal exposures lasting for minutes or hours. This is often referred to as "blue light hazard."

In the past, an assortment of optical filtering devices have been developed in an attempt to provide protection for the human eye from exposure to potentially damaging radiation at varying wavelengths. Matsushita (U.S. Pat. No. 5,922,246) describes a didymium-like organic dye in a compound which is compatible with a resin base material, resulting in a protective optical device that has a transmittance of not less 15% over the 590 to 660 nanometer range. U.S. Pat. No. 5,949,518 discloses a device with a polymer matrix, dye, and UV absorber coating, which absorbs in the 290 to 380 nanometer range.

The Gallas Patent 4,698,374 shows a photochromic lens system in which a layer of melanin pigment functions as an absorbent across the broad spectrum of UV, visible, and near IR wavelengths. U.S. Pat. No. 4,320,939 discloses a light-filtering optical system in which the filter element contains stable fluorescent dyes such as oxazine, carbazine, and carbopyronin. This combination absorbs across a wide variation from about 10% to about 99%, in a wavelength range of about 400 to 700 nanometers.

While these optical systems may all provide adequate eye protection for a specific use at varying ranges of wavelengths, there exists a need for a lens that significantly reduces or eliminates the transmission of the most damaging wavelengths, particularly in ranges between 570 and 610 nanometers.

The present invention consists of industrial protective eyewear lens combinations which significantly reduce or eliminate the transmission of certain eye-damaging ultraviolet and infrared radiation. As a result, the vision of the lens wearer is not impaired, and the wearer is able to more readily visualize his or her work while specific troublesome wavelengths are being filtered out.

SUMMARY OF THE INVENTION

It is therefore an object of the present invention to provide a protective eyewear lens system which prevents transmission of virtually all damaging radiation, particularly in a wavelength range of about 570 to 610 nanometers.

It is a further object of the present invention to provide a protective eyewear lens system which prevents transmission of at least 80% of damaging radiation, particularly in a wavelength range of 480 to 550 nanometers.

Other and further objects of the present invention will become apparent to those skilled in the art upon a study of the following specification, appended claims, and accompanying drawings.

BRIEF DESCRIPTION OF THE DRAWINGS

FIG. 1 is a diagrammatic cross-sectional view of the composite lens AGW-186, consisting of the S-8817-A filter material and the infra-red (IR) absorbing substrate;

FIG. 2 is a diagrammatic cross-sectional view of the composite lens AGW-200, consisting of the S-8817-A filter material and the Green Welding glass substrate;

FIG. 3 is a diagrammatic cross-sectional view of the composite lens AGW-286, consisting of the S-8817-A filter material, the infra-red (IR) absorbing substrate, and the Green Welding glass substrate;

DESCRIPTION OF PREFERRED EMBODIMENTS

Figure 4:
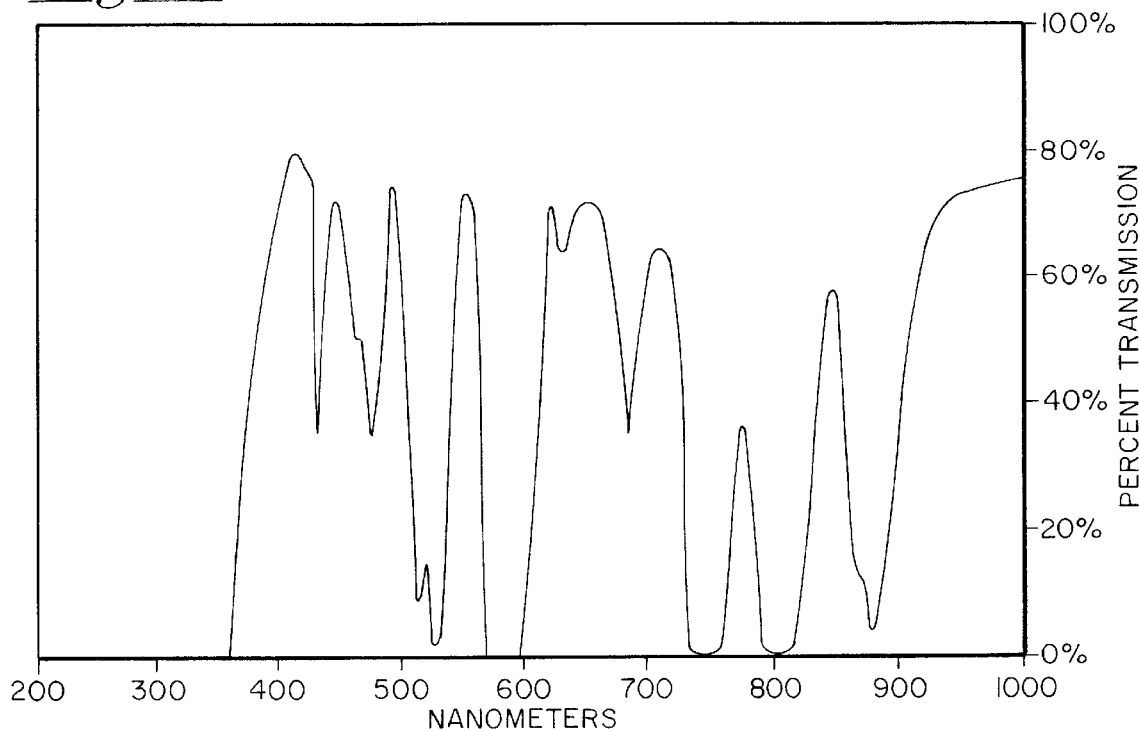
FIG. 4 is a graph illustrating the spectral transmittance of the S-8817-A ACE (Amethyst Color Enhancement) filter glass material.

For a more thorough understanding of the invention, refer now to the following detailed description with reference to the accompanying drawings, wherein a single Figure shows a cross-section of a composite lens according to an alternate preferred embodiment of the present invention.

As shown in FIG. 1, the dual-member AGW-186 composite lens 10 of the present invention consists of one element of S-8817-A substrate filter material 12 bonded to a second substrate filter material of infra-red (IR) absorbing glass 14. To produce the lens as shown in the accompanying drawing, a convex surface of base material Schott S-8817-A ACE (Amethyst Color Enhancement) glass is cemented to the concave surface of IR absorbing glass using a UV-curable adhesive. A variety of glass may be used, such as Schott KG-3 or KG-5, or Isuzu ISK-167 or ISK-171, according to availability. After curing, the composite lens is blocked, edged, and safety blocked prior to insertion into an ophthalmic frame.

FIG. 2 discloses the dual-member AGW-200 composite lens 16, which is composed of the S-8817-A filter material 12 laminated to one of either Shade 4 or Shade 5 Green Welding glass 18. As the Green Welding glass is available only in flat sheet, it must be exposed to a heat-slump operation to form the prerequisite lens shape or configuration, prior to curing, blocking, and edging. In finishing, the lens is blocked with the lamination line 8 millimeters above the center of the lens.

As illustrated in FIG. 3, the tri-member AGW-286 composite lens 20 uses substrates of the IR filter material 14, Green Welding glass 18, and S-8817-A 12. In assembly, the convex surface of S-8817-A and the concave surfaces of the IR filter lens and the Green Welding lens are aligned, and bonded using UV cure optical cement. In finishing, the composite lens is blocked with the lamination line 5 millimeters above the center of the lens, using a two-sided adhesive pad and metal blocking disc.

The S-8817-A base material is manufactured by grinding the convex surface of the lens blank, followed by curve generation of a concave surface to form a lens that has a matching negative curvature with the front lens. The lens is generated with a thickness to match safety standards. The manufacturing process of the IR absorbing glass and the Green Welding glass is the same as for the S-8817-A base material, except the finished thickness of the lens is selected to match "dress" or "street" standards.

The performance of the composite lens embodiments was tested using a Varian Cary 5E UV-VIS-IR spectrophotometer, with the results set forth in the transmission spectra in FIGS. 4–8.

FIG. 4 illustrates the transmission spectrum of the S-8817-A glass, with a significant reduction of radiation transmitted between 480 and 550 nanometers. Virtually 0% transmittance is seen between 570 and 610 nanometers, where incident radiation is most annoying to the human eye.

Figure 5:
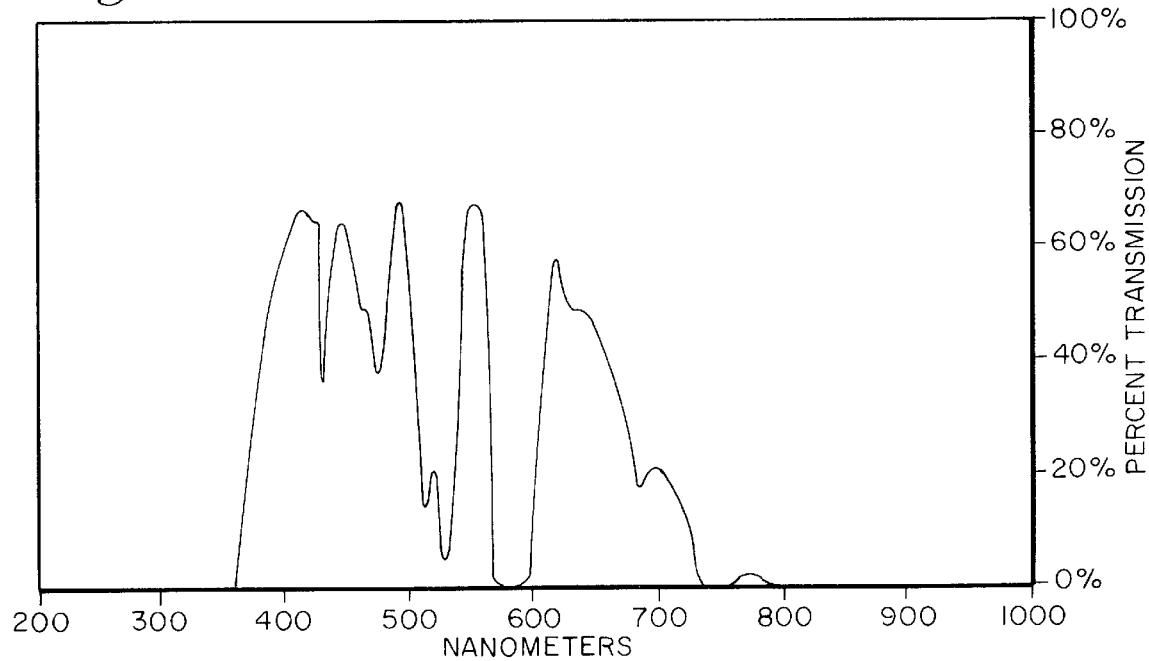
FIG. 5 is a graph illustrating the spectral transmittance of the AGW-186 composite lens, consisting of the S-8817-A filter material along with a substrate material of infra-red (IR) absorbing glass.

As illustrated in FIG. 5, the AGW-186 lens composite of IR absorbing glass and the S-8177-A filter further reduces radiation transmission across the IR, UV and visible wavelengths to less than 70% overall, with virtually no transmission occurring between 570 and 610 nanometers.

Figure 6:
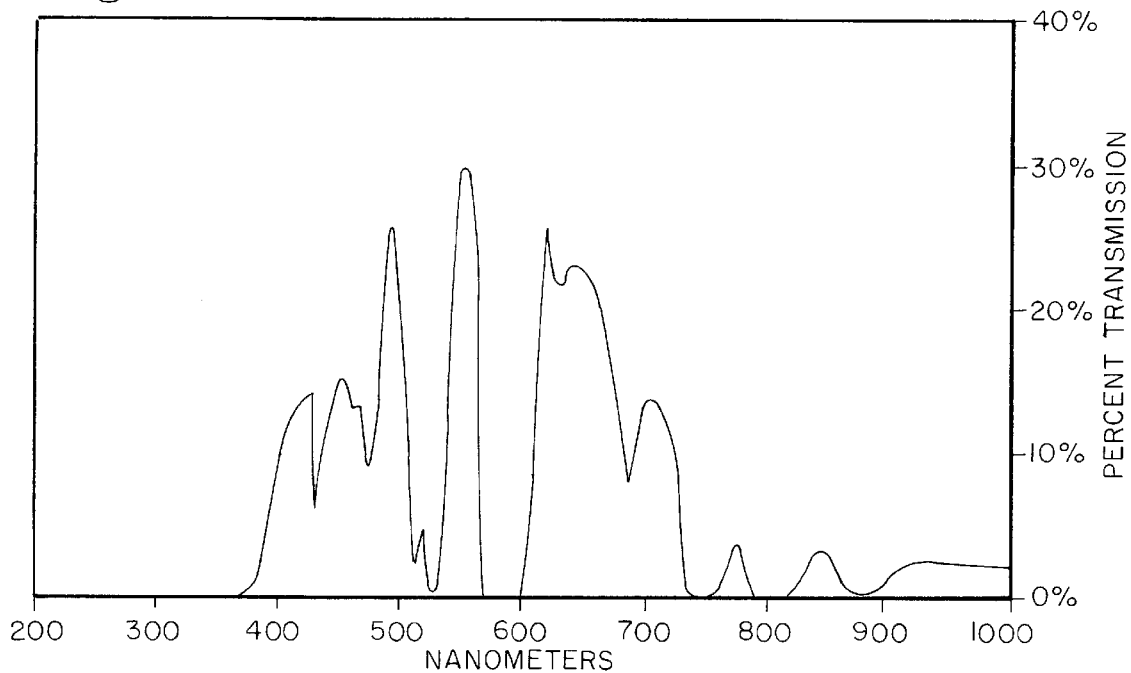
FIG. 6 is a graph illustrating the spectral transmittance of the AGW-200 combination lens, consisting of the S-8817-A filter material along with a substrate material of either Shade 4 or Shade 5 Green Welding glass.

In FIG. 6, the AGW-200 lens combination demonstrates a significant overall reduction in transmission of under 30%, with virtually no transmission occurring between 570 and 610 nanometers. The 3-membered combination lens system of AGW-286 possesses the transmission spectra of both the AGW-186 and the AGW200.

Figure 7:
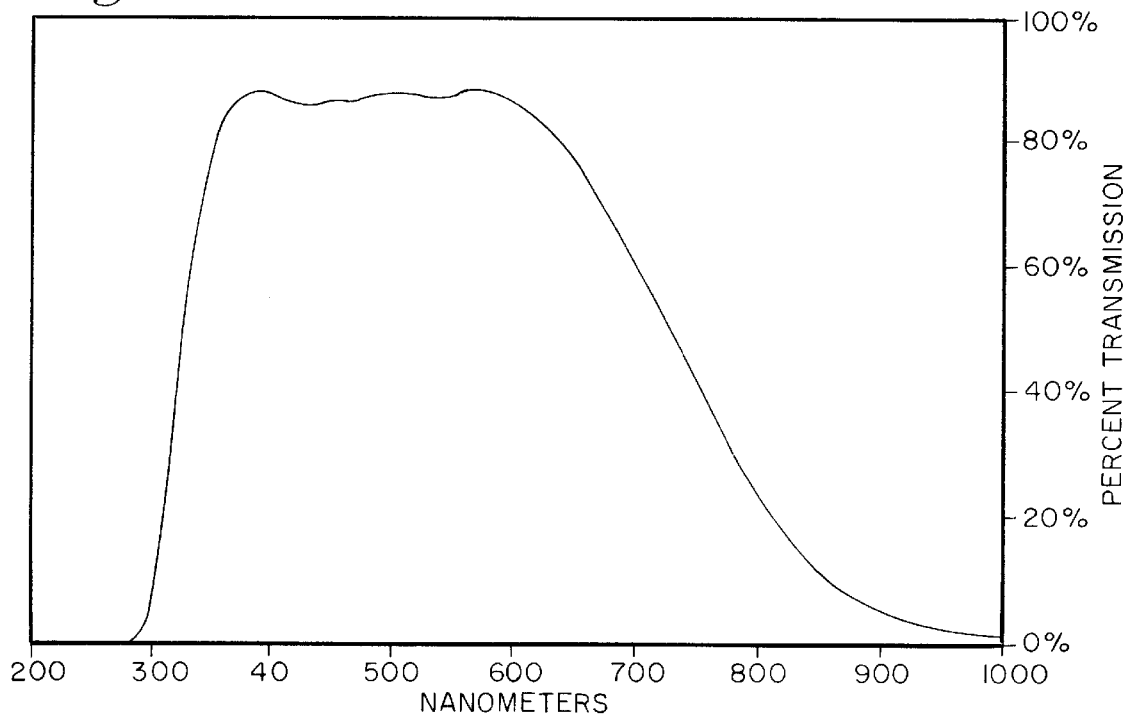
FIG. 7 is a graph illustrating the spectral transmittance of the substrate material of infra-red (IR) absorbing glass.
Figure 8:
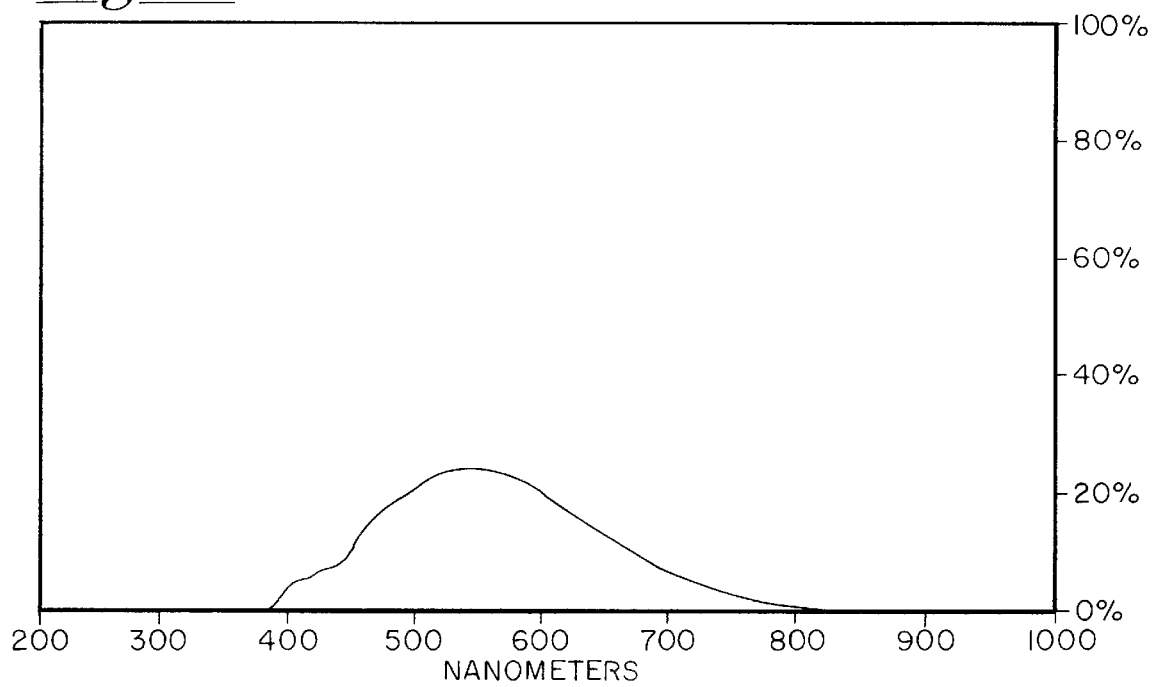
FIG. 8 is a graph illustrating the spectral transmittance of the substrate material of either Shade 4 or Shade 5 Green Welding glass.

As a contrasting control, FIG. 7 shows the transmission spectrum of the IR absorbing filter alone, with an overall transmittance of about 90%. FIG. 8 illustrates an overall transmission of less than 20% across the 400 to 800 wavelength range.

It will be appreciated that the examples set forth herein are for purposes of illustration only and are not intended as a limitation upon the scope of the appended claims.

What is claimed is:

1. An industrial safety glass system for reducing transmission of certain ultraviolet and infrared radiation, comprising a combination of lens means including distinct glass lens components bonded together to form a laminate and wherein the laminate comprises:

(a) a first concave glass lens component comprising a substrate transmissive to visible radiation and with a density effective for reduction of overall light transmission, said first lens component absorbing substantially all radiation in the range of between 570 nm and 610 nm, and absorbing a significant portion of radiation in the range of between 480 nm and 550 nm:

(b) a second glass lens component having a concave configuration complementary to said first concave glass lens component and consisting of infrared radiation absorbing glass.

2. An industrial safety glass system according to claim 1 in which said lens means is selected from group consisting of amethyst color enhancement glass, Shade 4 Green Welding glass and Shade 5 Green Welding glass.

3. An industrial safety glass system according to claim 1 wherein said lens means is an optical lens.

4. An industrial safety glass system according to claim 1 wherein said first and second glass lens components are bonded together with a UV-curable adhesive.

5. An industrial safety glass system according to claim 1 wherein the radius of curvature of said first lens equals the radius of curvature of said second lens.

6. The industrial safety glass system according to claim 1, wherein said second glass lens component is absorbative to radiation in the range of between about 780 and 1400 nm.

* * * * *